United States Patent [19]

Fischer

[11] Patent Number: Plant 6,800

[45] Date of Patent: May 16, 1989

[54] AFRICAN VIOLET PLANT NAMED HEIDRUN

[76] Inventor: Arnold Fischer, Kahlendamm 22, 3000 Hannover 51, Fed. Rep. of Germany

[21] Appl. No.: 130,199

[22] Filed: Dec. 8, 1987

[51] Int. Cl.[4] ..... A01H 5/00
[52] U.S. Cl. ..... Plt./69
[58] Field of Search ..... Plt./69

*Primary Examiner*—James R. Feyrer
*Attorney, Agent, or Firm*—Foley & Lardner, Schwartz, Jeffery, Schwaab, Mack, Blumenthal & Evans

[57] ABSTRACT

An African violet named Heidrun, having bright pink single flowers carried on strong upright peduncles above medium green foliage, compact rosette growth habit, and its floriferous habit, with flowering continuing for many weeks after the onset of flowering.

1 Drawing Sheet

1

The present invention comprises a new and distinct cultivar of African violet plant, botanically known as *Saintpaulia ionantha,* and hereinafter referred to by the cultivar name Heidrun.

The new cultivar was referred to during the breeding and selection process by the designation 81-5 and is a product of a planned breeding program. The basic objective of the breeding program was to create a new African violet cultivar having an abundance of bright pink, single flowers on upright peduncles, medium green foliage and compact growth habit.

The new cultivar was originated from a cross made by me in a controlled breeding program in Hannover, Federal Republic of Germany. Both the male and female parents are unknown at this time.

Heidrun was discovered and selected by me as a flowering plant within the progeny of the stated cross in a controlled environment in 1981 in Hannover, Federal Republic of Germany. Asexual reproduction of the new cultivar by leaf cuttings, as performed by me at Parrish, Fla., has demonstrated that the combination of characteristics as herein disclosed for the new cultivar are firmly fixed and retained through successive generations of asexual reproduction.

Heidrun has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Heidrun which in combination distinguish this African violet as a new and distinct cultivar:

(1) Bright pink single zygomorphic rotate flowers with very slightly ruffled margins and which are 30–35 mm in diameter.
(2) Medium green pubescent foliage, oval shaped with repand margins, cordate base and a broadly acute apex.
(3) Compact rosette habit with flowers held erect above the foliage on strong upright peduncles.
(4) Very floriferous, with flowers continuing to open for many weeks after the onset of flowering.

2

(5) Suitable for production in 10 cm pots, finishing in 9–13 weeks when started from 2¼" plantlet.

The new cultivar is most similar to Pink Lady, disclosed in U.S. Plant Pat. No. 5,065. Heidrun is principally distinguished from Pink Lady by its less deeply veined foliage and smaller flower size.

The accompanying color photographic drawing shows a typical specimen plant of the new cultivar. The photograph is in black and white, with several flowers being colored to accurately depict true flower color.

In the following description, color references are made to The Royal Horticultural Society Colour Chart (R.H.S.), except where general colors of ordinary significance are referrred to. Color values were taken under fluorescent light conditions at approximately 4:00 p.m. in Parrish, Fla.

Botanical classification: *Saintpaulia ionantha,* Ramat., cv. Heidrun.

Parentage: Unknown.

Propagation: The new cultivar holds its distinguishing characteristics through successive propagations by leaf cuttings.

Plant: From 6 to 10 cm tall when grown in pots, and approximately 20 cm in diameter when fully grown. The growth rate is vigorous, and the general shape of the fully grown plant is round.

*Leaves.*—Quantity: Abundant. Shape: Oval with repand margins. Diameter: Up to 8 cm on fully expanded leaves. Texture: Pubescent, glossy. Ribs and veins: Pinnate. Color (Upperside): 137A. Color (Underside): Solid 138D or solid 186A or a mixture of both. Stems: Purplish-green.

*Flowers.*—Buds: Size: About 1 cm×1 cm. Shape: Round. Rate of opening: Normal. Sepals: Shape: Lanceolate. Color: 183A. Phyllaries: 2, lanceolate. Color: Purplish-green. Calyx: Shape: Funnel. Size: 8–10 mm in diameter. Aspect: Pubescent. Peduncle: Length: 4–10 cm. Character: Erect, rigid. Color: Purplish-green.

*Individual flowers.*—Number of petals: 5. Size: 30–35 mm in diameter and 10 mm deep. Shape: Cup-shaped when bloom first opens, becoming flat as bloom matures. Color (upper side): 78D. Color (under side): 75B. Flowers fade slightly as they age. Flower color can vary due to amount of light, fertilizer, temperature and other growing conditions. Borne: Cymose clusters on upright peduncles. Flowering habit: Flowers profusely and intermittently year round with blooms lasting 2–3 weeks after which petals dry up but do not drop; finishes in 9–12 weeks when a $2\frac{1}{4}''$ plantlet is grown in a 10 cm pot.

*Reproductive organs.*—Stamens: Stamen borne singly on one side of ovary; 2 anthers basifixed. Anthers: 2 mm×2 mm, yellow. Filaments: 2–3 mm long, yellow with purple streaks. Pollen color: Yellow. Pistels: Number: 1. Styles: 1, 6 mm long. Stigma: Sticky, white. Ovaries: Superior. Roots: Fibrous and fine.

Disease resistance: No African violet diseases observed to date.

I claim:

1. A new and distinct cultivar of African violet named Heidrun, as illustrated and described.

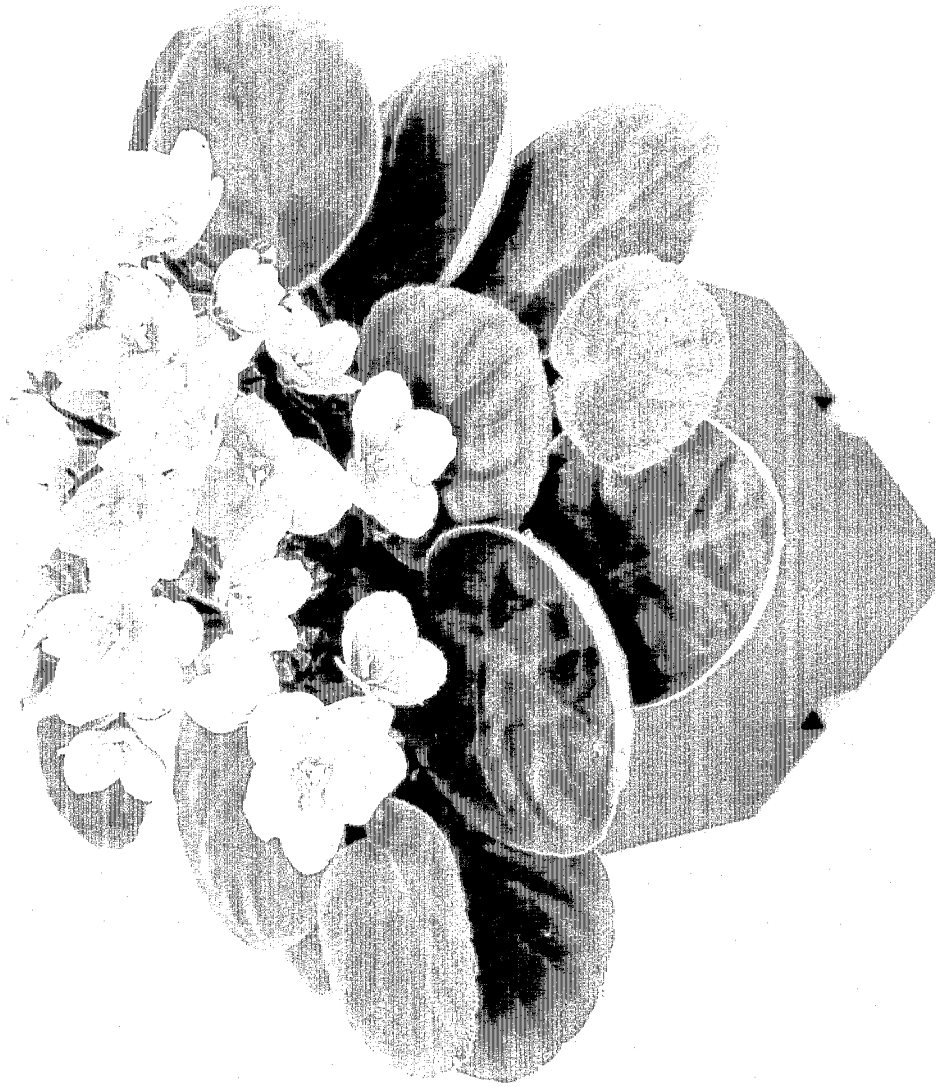

* * * * *